United States Patent [19]
Hoover

[11] Patent Number: 6,076,011
[45] Date of Patent: Jun. 13, 2000

[54] ELECTROMYOGRAPHIC FEEDBACK MONITOR SYSTEM

[75] Inventor: Jan C. Hoover, Bainbridge, Wash.

[73] Assignee: J&J Engineering, Poulsbo, Wash.

[21] Appl. No.: 09/252,606

[22] Filed: Feb. 2, 1999

[51] Int. Cl.⁷ .................................................. A61B 5/04
[52] U.S. Cl. ....................................................... 600/546
[58] Field of Search ............................................ 600/546

[56] References Cited

U.S. PATENT DOCUMENTS

| | | | |
|---|---|---|---|
| 3,898,983 | 8/1975 | Elam | 128/2 N |
| 3,905,355 | 9/1975 | Brudny | 128/2.1 M |
| 3,920,003 | 11/1975 | Ash et al. | 128/2.1 Z |
| 3,924,609 | 12/1975 | Friedenberg et al. | 128/2.1 R |
| 3,933,147 | 1/1976 | Du Vall et al. | 128/2 S |
| 4,396,019 | 8/1983 | Perry, Jr. | 128/733 |
| 4,801,921 | 1/1989 | Zigenfus | 340/573 |
| 4,811,742 | 3/1989 | Hassel et al. | 128/733 |
| 5,291,902 | 3/1994 | Carman | 607/138 |
| 5,411,548 | 5/1995 | Carman | 607/138 |
| 5,785,666 | 7/1998 | Costello et al. | 600/546 |

*Primary Examiner*—Scott M. Getzow
*Attorney, Agent, or Firm*—George C. Rondeau, Jr.; Brian L. Johnson; Seed IP Law Group, PLLC

[57] ABSTRACT

A system to monitor surface electromyographic (EMG) activity of a user and provide appropriate feedback to the user includes an EMG feedback monitor sized and configured to be worn by the user. In the depicted embodiment, surface EMG activity is measured with electrodes integrally affixed to a housing of the system. Feedback is typically provided using vibrations of certain duration and repetition. The system operates under various user selectable operational modes. Each operational mode is associated with particular electromyographic feedback criteria used to determine appropriate feedback for the user. The electromyographic feedback criteria is related to signal levels and time measurements associated with surface EMG activity level measured of the user. The depicted embodiment includes a computer interface allowing EMG signal data recorded by the EMG feedback monitor to be sent to a computer system. The computer system is also used to adjust and download desired operational modes into the EMG feedback monitor.

36 Claims, 8 Drawing Sheets

ELECTROMYOGRAPHIC FEEDBACK MONITOR SYSTEM

TECHNICAL FIELD

The invention relates to physiological monitoring systems and, more particularly, to a wearable electromyographic feedback monitor system. The present invention is related to commonly assigned, concurrently filed and co-pending U.S. application Ser. No. 09/243,094 for "Respiration Feedback Monitor System;" and U.S. application Ser. No. 09/243,230 for "Heart Rate Variability Feedback Monitor System."

BACKGROUND OF THE INVENTION

Electromyographic (EMG) activity at various locations on the skin surface of an individual person is an indicator of many physiological conditions related to the individual's level of fitness or health. Through muscle activity, weak electrical currents are generated. An EMG signal is measured from these currents in a microvolt range having a frequency range of 20 to 400 Hz. The EMG signal measurement is taken on the surface of the individual using electrodes of a certain impedance.

Many examples of how EMG signal measurement correlates to health and fitness conditions involve repetitive motions including such activities as typing or manufacturing assembly with repetitive motion involving wrists, hands, arms, and shoulders. These repetitive motions may all cause health problems if done improperly. Studies have shown that those that properly undertake repetitive motion take brief rests that are oftentimes unnoticeable to the trained eye. Fortunately, activity with repetitive motion interrupted by brief rests has corresponding surface EMG activity with recognizable patterns related to signal strength versus time measurements. Attempts have been made to use these patterns to train individuals to properly practice repetitive motions to either unlearn or avoid improper habits. The effectiveness of prior art systems unfortunately has been limited due to restrictions imposed by these systems. For instance, users are restricted to certain locations and activities by the prior art systems. Also, the devices and methods providing feedback to users are cumbersome and indirect so that the prior art systems do not provide the type of demonstrative and meaningful feedback to dramatically encourage positive changes in behavior by the users.

Posture is another area in which surface EMG activity has been used with limited success to help correct conditions. Those with proper posture have certain surface EMG activity patterns at certain locations on the surface of their body, whereas those with improper posture have other patterns at the same locations. The limited success again has been due to prior art systems. The effort required to use prior art systems is as great or greater than that required to modify behavior. Oftentimes, the extra burden is too much for a user to reach desired goals and health benefits. Other situations conductive to surface EMG activity monitoring involve bruxism. Here an individual grinds their teeth while sleeping so has little awareness by natural means of the problem while it is occurring. Headaches, neck and shoulder pain, back pain, and other states of inappropriate muscle activation causing pain or muscle problem are also candidates for monitoring surface EMG activity.

Prior art devices which monitor surface EMG activity and provide feedback place unnecessary demands on users and furnish inadequate feedback. Typically, an individual being monitored by a prior art device will go to a clinic or other location such as their home where an EMG feedback monitor is located. For instance, U.S. Pat. Nos. 5,291,902 and 5,411,548 to Carmen teach methods for incontinence treatment and treatment of other health conditions. The methods are practiced in designated exercise sessions limited typically to a location in the home. The limited accessibility of prior art EMG feedback monitors affords little opportunity for training. Also, the feedback used is only indirectly associated with the regions of concern on the user's body, so is of limited value.

SUMMARY OF THE INVENTION

The invention overcomes the limitations of the prior art and provides additional benefits by providing an electromyographic feedback monitor system. The electromyographic feedback monitor allows for expanded accessibility under a wide range of activities. As part of the feedback provided, the electromyographic feedback monitor furnishes effective feedback that is directly related to areas of concern. The feedback is also discrete in nature. This in addition to other aspects of the invention provides effective, discrete, and timely electromyographic monitoring and feedback without being overly burdensome. Thus, the invention overcomes the problems and difficulties posed by the prior art systems and provides numerous additional benefits.

Aspects of the invention are directed to an electromyographic feedback monitor system for a user. An aspect of the invention includes a sensor package sized and configured to be worn by the user. A plurality of electrodes affixed to the sensor package are configured to produce electromyographic signals based on surface electromyographic activity of a monitored region of the user. A vibration output device affixed to the sensor package is configured to transmit to the monitored region of the user a vibration signal perceptible by the user when the output device is activated. A processor is configured to receive digital signals associated with the electromyographic signals produced by the plurality of electromyographic electrodes which measure the electromyographic activity of the user. The processor is configured to transmit a signal to activate the vibration output device based on whether the measured electromyographic signals satisfy electromyographic feedback criteria wherein the electromyographic feedback criteria are related to electromyographic signal levels and time measurements associated with the measured electromyographic signals. A user control coupled to the processor allows a user to select an operational mode having particular electromyographic feedback criteria from a plurality of operational modes under which the processor operates.

In another aspect of the invention, the sensor package is an integral part of a housing. The vibration output device and the processor are affixed to the housing. In a further aspect of the invention, a housing is sized and configured to contain the processor and user control. The processor is further configured to adjust the electromyographic feedback criteria of the selected operational mode based on the electromyographic signals. The of operational modes include Percent Time Amplitude Mode, Threshold Amplitude Mode, Media Frequency Mode, Prompted Exercise Mode or Threshold Shaping Mode. A slave output is electrically coupled to the processor by an electrical cable external to the housing in one aspect and by a wireless communication link in another aspect of the invention.

As is conventional in the field of electrical circuit representation, sizes of electrical components are not drawn to scale and various components are enlarged or reduced to improve drawing legibility. Component details have been abstracted in the Figures to exclude detail such as position of components and precise connections used between components.

DETAILED DESCRIPTION OF THE INVENTION

A feedback monitor, and in particular, an apparatus and corresponding method for a electromyographic (EMG) feedback monitor system for monitoring EMG activity of surface locations on a user's body is described in detail below. In the following description, numerous specific details are provided, such as specific configuration of the apparatus, circuit components, ways of wearing the EMG feedback monitor, EMG criteria used for feedback, etc., to provide a thorough understanding of the embodiments of the invention. One skilled in the relevant art, however, will recognize that the invention can be practiced without one or more of the specific details or with other processes, configurations, hardware, etc. In other instances, well-known structures or operations are not shown or described in detail to avoid obscuring the description of the embodiments.

Each of the circuits whose function and interconnection is described in connection with FIGS. 1–5 and 7–8 is of a type known in the art, and one skilled in the art would be able to use such circuits in the described combination to practice the invention. The internal details of these particular circuits are not part of, nor critical to, the invention. Therefore, a detailed description of the internal circuit operation is not required. Similarly, each of the steps depicted in FIG. 6 is of a type well known in the art and may itself include a sequence of operations which need not be described herein.

The depicted embodiment of the invention solves problems of prior art EMG feedback monitors. The prior art EMG feedback monitors are burdensome to use and provide insufficient feedback. The depicted embodiment is lightweight and compact, along with other characteristics, so can be worn throughout the day. Also, the depicted embodiment is simple to operate, which promotes ease of use. Further, the depicted embodiment has a feedback mechanism that is discrete allowing use of the wearable EMG feedback monitor in most situations and environments common to everyday life. Also, the feedback mechanism does not require attention to be directed toward the feedback mechanism, while users wait for feedback. The depicted embodiment region is far less distracting to users and allows users to better practice the activities of concern. Direct feedback is applied to the region of concern on a user. This dramatically increases the amount of positive feedback to the user by directly associating the feedback stimulus with the region of concern on the user's body. All these features of the depicted embodiment are in sharp contrast to the prior art systems, which were limited to certain locations and environments and hindered users from practicing activities of concern during monitoring. Given the ease of use and great range of locations and environments in which the depicted embodiment can be used, users are afforded the appropriate amount of feedback regarding their surface EMG activity to allow them to take measures to correct or improve health and fitness conditions.

Figure 1:
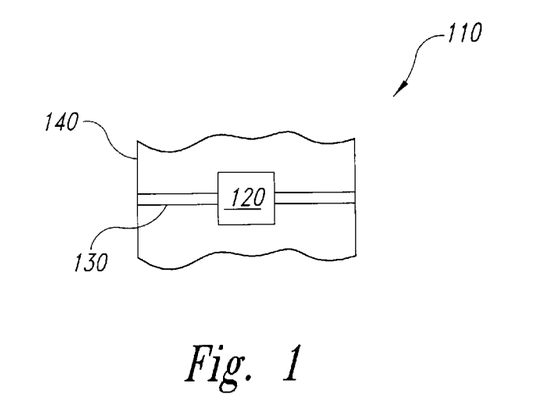
FIG. 1 illustrates an embodiment of the invention in use.

In order to monitor surface EMG activity levels continually throughout the day, a user ideally should wear an EMG feedback monitor. In this way, the EMG feedback monitor travels with the user rather than the user having to travel to the EMG feedback monitor. The depicted embodiment is small and lightweight enough to be wearable in many positions, locations, and configurations including in the vicinity of limbs, torso, head or neck, or other parts of the body. In the depicted embodiment, an EMG feedback monitor 110 includes a housing 120 and a strap 130 to secure the EMG feedback monitor to a portion of a surface of a user 140 as shown in FIG. 1. The EMG feedback monitor 110 is worn next to the skin and under the clothes of the user 140 to monitor surface EMG activity of the user. The EMG feedback monitor 110 can thus be worn unobtrusively during normal activities. The EMG feedback monitor 110 in other embodiments is secured to the user 140 through the use of clothing or is worn over clothing either in addition to or separate from the strap 130. One skilled in the art will recognize that there are many ways to wear the EMG feedback monitor 110 given its small, compact size. The ways depicted in the present embodiments are not intended to limit in any way how the EMG feedback monitor 110 is to be worn.

Figure 2:
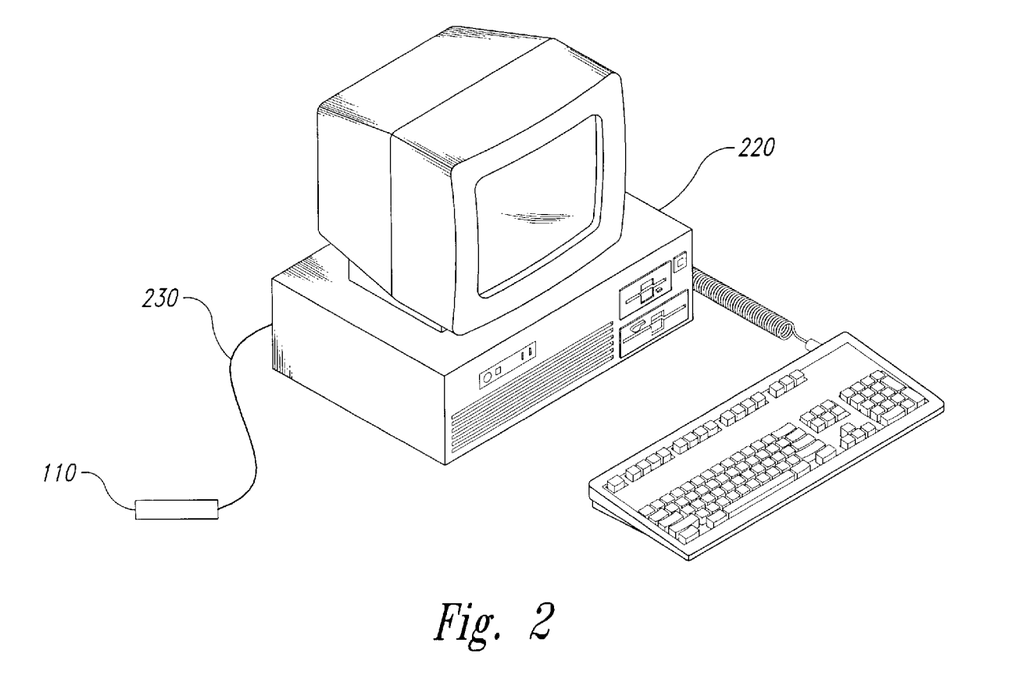
FIG. 2 illustrates the embodiment of FIG. 1 connected to a computer system.

As will be discussed in further detail below, the EMG feedback monitor 110 communicates with a computer system 220 over a computer interface cable 230, as shown in FIG. 2. One end of the computer interface cable 230 has an optical isolation module that provides electrical safety and connection compatibility with a communication port of the computer system 220. Alternative embodiments use other communication links instead of the computer interface cable 230. These other communication links include wireless links or optical fiber links. The computer system 220 is used to program the EMG feedback monitor 110 and also to analyze historical data stored in the EMG feedback monitor related to surface EMG activity of a user such as the user 140. The computer system 220 is thus used to track progress regarding therapeutic intervention or treatment associated with training. Based on the extent of progress that the user experiences, a therapist in the depicted embodiment will adjust or replace criteria used by the EMG feedback monitor 110 to train the user 140 as explained further below. Connection with the computer system 220 via the computer interface cable 230 is typically only an occasional event. Typically, the user 140 more frequently wears the EMG feedback monitor 110 without the EMG feedback monitor being connected to any other type of device.

The computer system 220 executes software that provides several capabilities. The software allows a particular feedback mode to be associated with an EMG feedback monitor control setting and the levels or thresholds and other parameters to be selected for that particular mode. The software can read EMG signal data collected by the computer system 220 from the EMG feedback monitor and cause the data to be displayed such as in graph form on a display of the computer system 220. The software can also store the EMG signal data to appropriate patient/user record files. The software can recall previously stored EMG signal data and produce summary reports of training progress. The software allows visual feedback if the EMG signals are provided to the computer system 220 live by the user 140. This is used to educate the user 140 regarding various feedback vibrations and thresholds for each mode. The software can also provide training information regarding use of the EMG feedback monitor 110.

Figure 3:
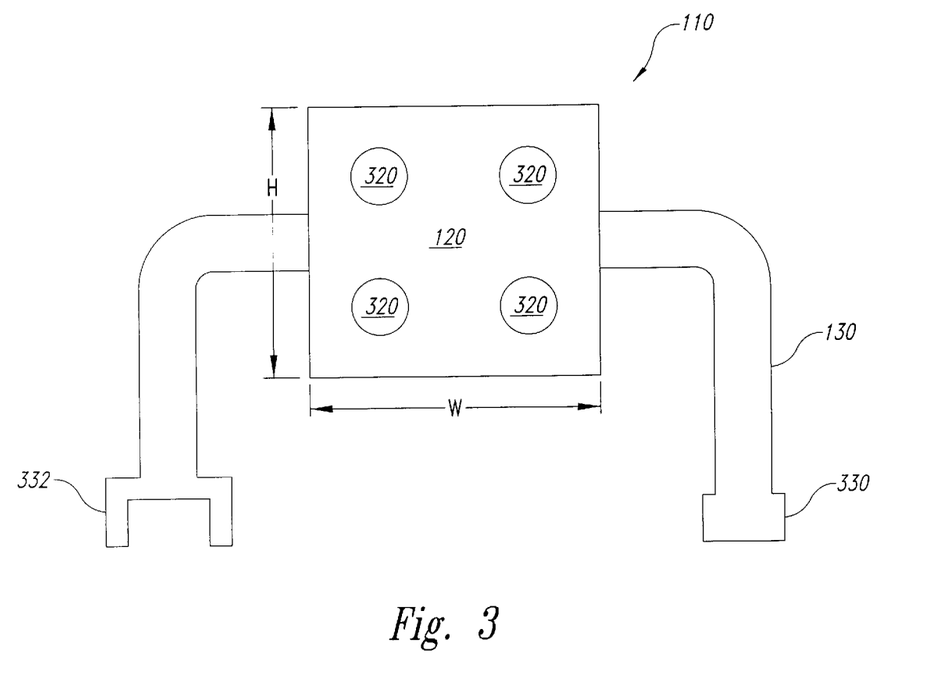
FIG. 3 is a top view of the embodiment of FIG. 1 showing positioning of the electrodes.

The EMG feedback monitor 110 also includes electrodes 320, shown in FIG. 3, that in the depicted embodiment are affixed to an underside of the housing 120. The electrodes 320 are positioned with respect to the housing 120 so that the EMG feedback monitor 110 may be secured to a portion of the user 140 with respective first and second portions 330 and 332 of a buckle secured to the strap 130. The electrodes 320 are positioned on the surface of the portion of the user 140 either against skin or clothing to measure surface EMG activity. In other embodiments, the electrodes 320 are not integrated into the housing 120 of the EMG feedback monitor 110. Instead, the electrodes 320 are detachably connected to the EMG feedback monitor 110 through a signal cable so that the electrodes can be positioned on the user 140 in a location other than where the EMG feedback monitor is positioned. The size of the housing is small, such as about 2 to 4 inches or smaller in height (H on FIG. 3) and about 2 to 8 inches or smaller in width (W on FIG. 3) and about ½ to 2 inches or smaller in depth (D on FIG. 3). Preferably, the housing is sized about 2¾ inches in height, about 2¼ inches in width and about ⅝ inches in depth. The housing size greatly contributes to the wearability of the EMG feedback monitor 110.

Figure 4:
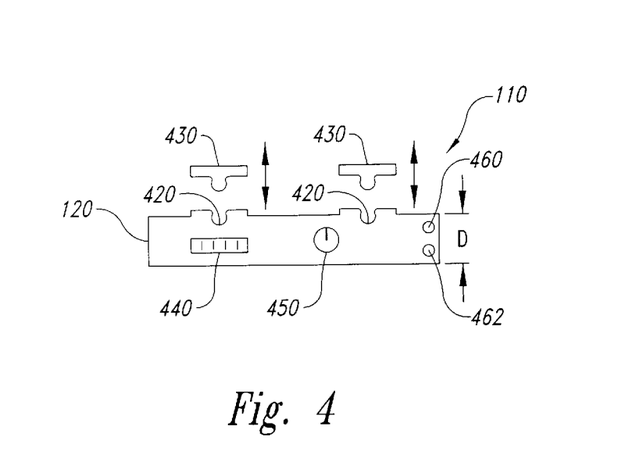
FIG. 4 is a side view of the embodiment of FIG. 1 showing a user control, computer interface connector, and indicator lights.

The EMG feedback monitor 110 also includes electrode snaps 420 configured in the underside of the housing 120, as shown in FIG. 4. The electrode snaps 420 receive disposable skin contact electrodes 430 in the depicted embodiment. The electrodes 430 are configured to be snap fit to, and removable from, the electrode snaps 420. A computer interface cable connector 440 is accessible from the housing 120 so that the computer interface cable 230 can be attached to the EMG feedback monitor 110 for communications to the computer system 220. A user control 450 is positioned on the housing 120 to allow a user to adjust EMG monitoring criteria as discussed further below. In the depicted embodiment, the user control 450 is a control knob, but other embodiments have other standard control input devices known in the art such as keypads and switches. Status indicator 460, typically a red light, and power indicator 462, typically a green light, convey status and power information discussed below to the user 140 about the current condition of the EMG feedback monitor 110. Devices other than lights such as LED displays, audio output devices or other devices known in the art to convey status and power information are used by other embodiments of the invention.

Figure 5:
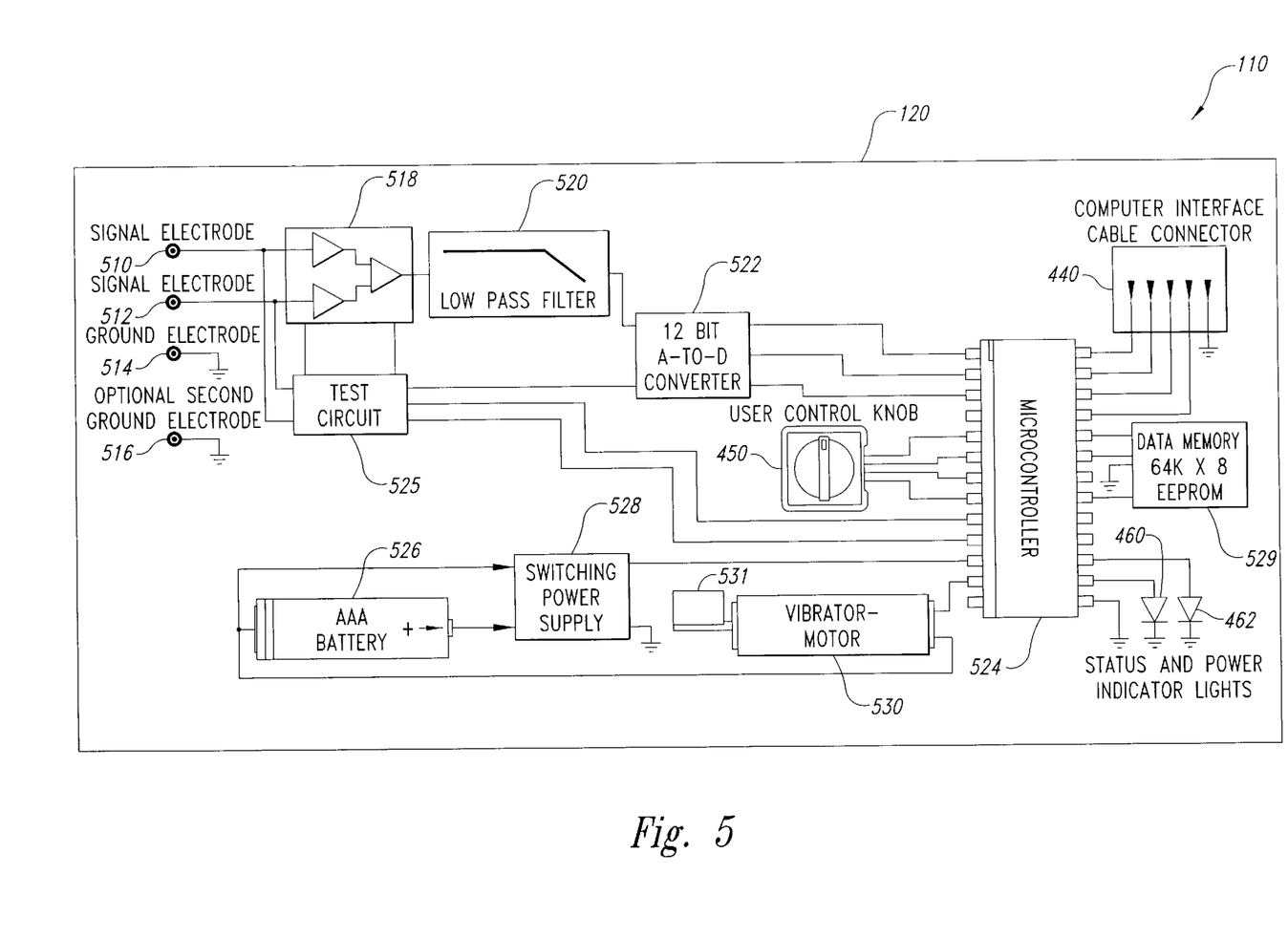
FIG. 5 is a block diagram of circuit details of the embodiment of the invention of FIG. 1.
Figure 6A:
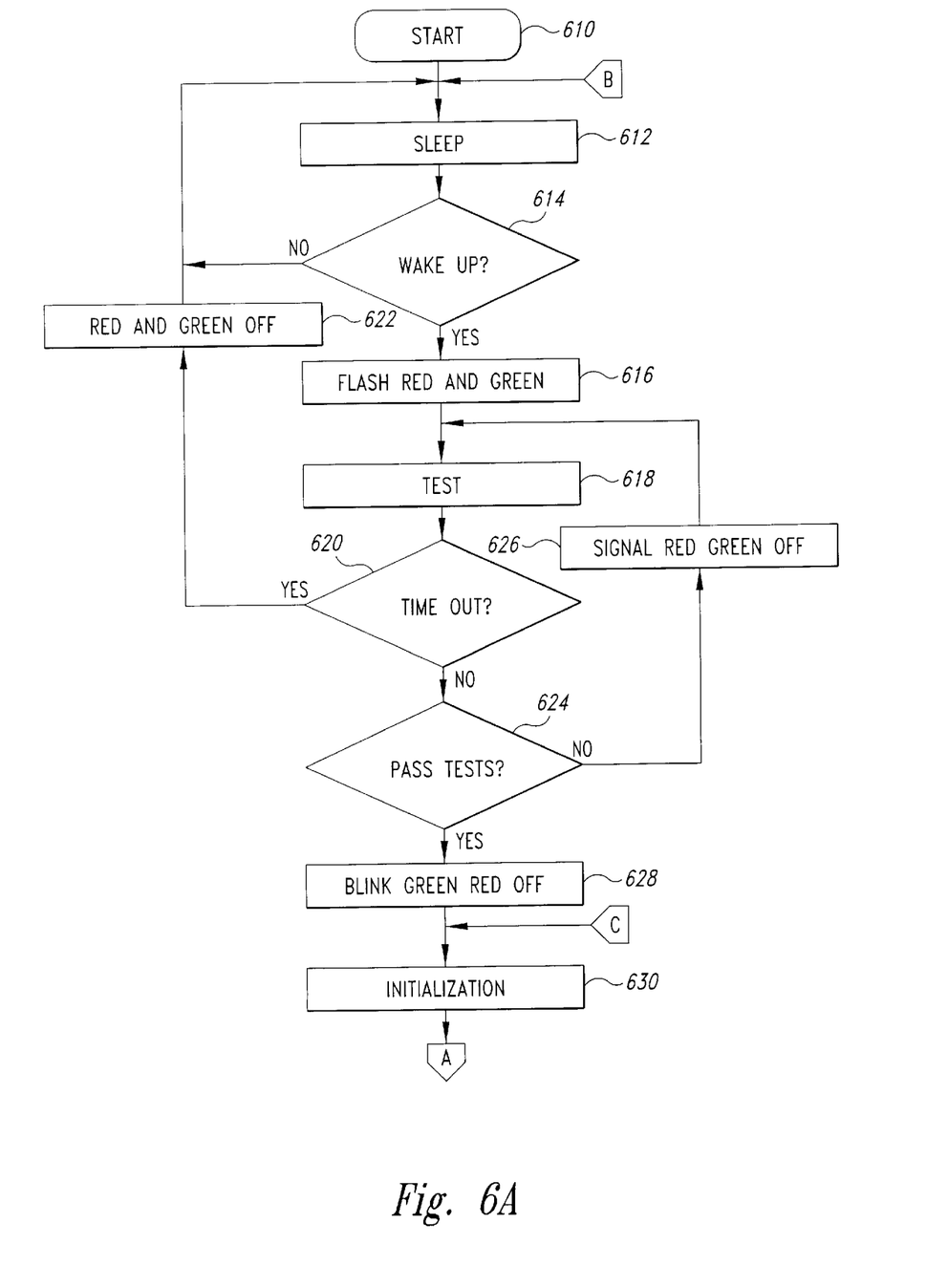
FIG. 6 is a flowchart of the process implemented by the microcontroller of the embodiment of FIG. 5.
Figure 6B:
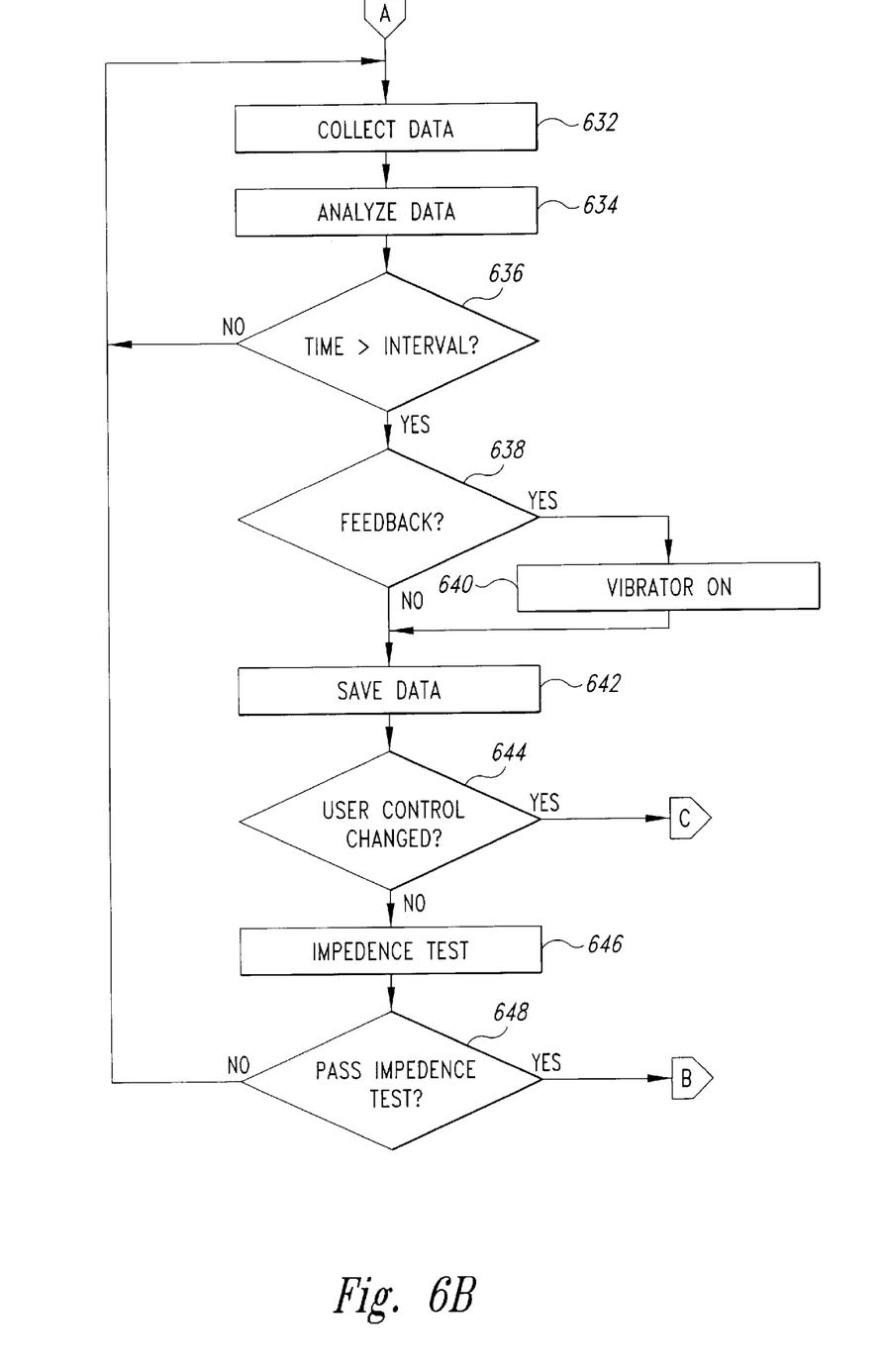

Further components of the EMG feedback monitor 110 for the depicted embodiment are shown in FIG. 5. The four electrodes 320 of FIG. 3 are shown in FIG. 5 as signal electrodes 510 and 512, a ground electrode 514 and an optional second ground electrode 516. The optional second ground electrode 516 is used for mechanical stability and to enhance reliability of the signals being measured. The signal electrodes 510 and 512 are electrically coupled to an input amplifier 518. Input amplifier 518 is a differential amplifier, which in the depicted embodiment has a gain of 250, self noise equal to 0.5, and common mode rejection equal to 100 dB, which are specifications known in the art to describe a differential amplifier. Other embodiments are not limited to these specific specifications of the input amplifier 518.

The input amplifier 518 amplifies the difference of the electrical signals provided by signal electrodes 510 and 512. This difference is then supplied to a low pass filter 520 which passes only low frequencies to a 12-bit analog to digital (A to D) converter 522. The low pass filter 520 is a 2-pole, 400 Hz filter to remove noise from the signal before being supplied to the A to D converter 522. In other embodiments, filters with other specifications are used appropriately to remove noise. The 12-bit A to D converter 522 then converts the signal provided by the low pass filter in analog form to digital form and passes the digitized signal in a serial manner to a microcontroller 524, also known as a processor. Test circuit 525 is electrically connected to the signal electrodes 510 and 512, the input amplifier 518, the low pass filter 520, the 12 bit A to D converter 522 and microcontroller 524 as shown in FIG. 5. The test circuit 525 performs tests on the various components of the EMG feedback monitor 110 as discussed below.

A power source 526, in the depicted embodiment shown as a AAA battery, provides the power for the EMG feedback monitor 110. The battery 526 is electrically coupled to a switching power supply 528 that converts power from the battery 526 to a stable 3.3 volt DC required by the circuitry of the microcontroller 524. Data memory 529 is electronically connected to the microcontroller 524 to furnish data and instructions to the microcontroller. In the depicted embodiment data memory 529 comprises a 64×8 EEPROM, however, any other data and instruction storage device known in the art is contemplated for other embodiments with size being a restriction upon selection. In other embodiments, the microcontroller 524 is monolithically integrated with the data memory 529 on a single integrated circuit chip. In further embodiments, other combinations including some of the input amplifier 518, low pass filter 520, 12 bit converter 522, switching power supply 528, and data memory 529 are monolithically integrated with the microcontroller 524 on a single integrated circuit chip. Additional embodiments locate the microcontroller 524 in a housing separate from where other components such as the input amplifier 518, low pass filter 520, A-to-D converter 522, and data memory 529 are located. In these embodiments, the microcontroller 524 communicates with these other components through a data link such as an electrical, optical, or wireless link.

A vibrator-motor 530 with weight 531 is activated by the microcontroller 524 to provide vibratory or tactile feedback to the user 140 when certain parameters are satisfied to generate a feedback event. These parameters are downloaded into the data memory 529 to program the EMG feedback monitor 110. These parameters are selected from preselected parameters, such as time that measured EMG activity stays above a specified threshold, maximum and minimum threshold levels for EMG activity to exceed and not to exceed, respectively, amount of time since the last feedback event, duration of feedback, percent of overall time that the EMG activity level is at a certain amplitude, and/or the amount of standard deviation or corrected standard deviation of the EMG activity level.

Alternative embodiments use distribution plots of EMG activity levels. Typically, the distributions are stored based on percentages of occurrences of EMG activity level that fall in designated ranges. Often, the EMG activity level for an occurrence is the user's EMG activity level averaged over the duration of time of the occurrence. With the alternative embodiments, the microcontroller 524 compares the user's EMG distribution plot with either model EMG distribution plots or the user's previous EMG distribution plots stored in data memory 529. Based on these comparisons, or combined with further conditions discussed below, the EMG feedback monitor 110 applies an appropriate level of feedback.

The user 140 selects entire sets of parameters associated with particular operational modes having individualized electromyographic feedback criteria with the user control knob 450 in the form of a rotary switch in the depicted embodiment. In this way, the EMG feedback monitor 110 can be used for different purposes or activity levels. For example, one setting would remind the user 140 not to overwork while typing and another setting would assist the user in relaxing. A physician or therapist would preset these sets of parameters based on clinical information, skill level of the user 140, and appropriate activity for the user 140. The therapist would then determine the appropriate setting and download several sets of parameters that would correspond to different rotary positions of the user control knob 450. The user 140 would be instructed regarding the settings of the user control knob 450. For instance, setting 1 could be used during typing, setting 2 could be used during lifting, setting 3 could be used during resting, etc.

The sets of parameters are downloaded into the EMG feedback monitor 110 from the computer system 220 over the computer interface cable 230 into the EMG feedback monitor. These parameters are used by the microcontroller 524 to analyze the digital signals provided by the A to D converter 522. Depending on the results of the analysis by the microcontroller 524, the data memory 529 stores certain historical data on surface EMG activity level of the user 140. Typically the therapist indicates which data and statistics are to be stored in the data memory 529 during programming of the EMG feedback monitor 110 when the parameters are downloaded from the computer system 220 into the EMG feedback monitor via the computer interface cable 230.

The parameters stored in data memory 529 may also be modified by the microcontroller 524 directly based upon past activity by the user 140. For example, the user 140 may select with the user control knob 450 feedback criteria so that for the entire time allotted for monitoring, feedback is given for only a certain selected percentage of time. The microcontroller 524 then adjusts and updates the threshold in order that feedback occurs at the selected percentage of time. For example, if the user selects feedback to occur an average of 25% of any given period of time, the microcontroller 524 would take previously recorded EMG activity level and adjust the threshold so that the user was in range 75% of the time and out of range 25% of the time. The microcontroller 524 of the EMG feedback monitor 110 would then give the appropriate amount of feedback. If performance of the user 140 subsequently changes, the microcontroller 524 adjusts the threshold appropriately so that the amount of feedback would still be 25% on average of the overall time for monitoring.

The EMG feedback monitor 110 in the depicted embodiment operates under other operational modes including Percent Time Amplitude, Threshold Amplitude, Medium Frequency and Prompted Exercise, each described below. Each mode can be operated either with fixed or adaptive thresholds. Adaptive thresholds change based on how the user progresses with his or her training. In the Percent Time Amplitude Mode, the microcontroller 524 determines the amount of time the EMG signal level is at various root mean square (RMS) amplitudes. Preset periods of time are typically generated by moving a preset window of time over the total monitoring time period. The EMG RMS amplitude is averaged for each window of time, which is typically an interval of 10 to 500 msec. An expected EMG RMS amplitude is divided into N bins, with the number of bins being preselected by the user. For each window of time the corresponding EMG RMS amplitude average is placed in its corresponding amplitude bin, providing a calculated percentage distribution and showing the percentage of time that the EMG signal was at each RMS amplitude. Feedback is given based on the calculated percentage associated with a certain bin or bins. The thresholds associated with each percentage distribution for each selected bin are independently adjustable.

For the Threshold Amplitude Mode, when the EMG RMS amplitude either goes above or below a preset threshold over a preset length of time feedback is given. Also, the repetition or duration of vibration in one embodiment is linear to the amount that the EMG signal amplitude exceeds a threshold. For example, when the threshold is exceeded by 200%, feedback is given twice as often or lasts twice as long as when the threshold is exceeded by 100%. In the Median Frequency Mode, a median frequency is determined from a spectral analysis by the microcontroller 524 over a given number of samples and a given time window. Median frequency shifts are detected as a percentage change over time or relative to a preset level. Feedback is given when the shift in median frequency exceeds either a percentage or level threshold.

For the Prompted Exercise Mode the user 140 is prompted to begin exercising with a vibration of short duration. The degree of success is then signaled by other vibratory patterns such as vibrations of long duration or multiple vibrations. For example, a patient who needs to strengthen a muscle may go to a therapist. The therapist determines that the patient can contract the muscle for 5 seconds to a surface EMG activity level of 15 microvolts and then rest for 10 seconds. The therapist determines that this should be repeated for 20 times. The therapist then downloads this set of parameters into the data memory 529 and assigns it to switch position 1 of the user control knob 450. Prior to an exercise session, the user then selects switch position number 1 of the user control knob 450. At the beginning of the exercise session, the user 140 receives a single vibration from the vibrator-motor 530 signaling the user to start contracting the designated muscle. During contraction of the muscle, when the user 140 exceeds the 15 microvolt surface activity level threshold and holds the surface EMG activity level above the 15 microvolt threshold for 5 seconds, the user then receives two short term vibrations from the vibrator-motor 530 signaling the user to relax. After a rest period of 10 seconds, the user receives another single vibration from the vibrator-motor 530 signaling the user to repeat the contraction exercise. These series of events repeat for the prescribed 20 times and then the EMG feedback monitor 110 turns off. Data related to this exercise session is saved in data memory 529 for future reference by the therapist.

The Threshold Shaping Mode provides alternative approaches in tailoring the amount of feedback based on the user's previous performance, established objectives, and the user's individual characteristics. One approach involves a goal threshold based on a present criteria downloaded by a therapist. The EMG feedback monitor 110 measures a current level of EMG activity and gives feedback based on the goal threshold and the current measured level of EMG activity. Next, the EMG feedback monitor 110 computes a median threshold between the current measured level of EMG and the goal threshold. If subsequent EMG activity levels satisfy the median threshold over a present period of time, the EMG feedback monitor 110 readjusts the median threshold toward the goal threshold, otherwise, the EMG feedback monitor maintains the median threshold and gives feedback. The EMG feedback monitor 110 gradually moves the median threshold toward the goal threshold as subsequent levels of EMG activity continue to satisfy the median threshold. However, if subsequent levels of EMG fail to satisfy the median threshold over a present period of time, the median threshold is readjusted toward the current level of EMG activity.

Under a second approach of the threshold shaping mode the microcontroller 524 first uses one or more feedback modes and procedures including those elaborated above to determine when feedback would be appropriate as a "feedback event." However, instead of administering feedback upon the occurrence of each feedback event, the microcontroller 524 counts these feedback events. With the second approach, feedback is not actually contingent solely upon a feedback event. Rather, the second approach involves additional conditions to be satisfied before feedback is given.

Under the second approach, the microcontroller 524 additionally determines one or more EMG distribution plots related to the user's EMG activity. These additional EMG distribution plots and/or values are in addition to EMG distribution plots and/or values that the microcontroller 524 may use to determine feedback events. The microcontroller 524 then compares the additional EMG distribution plots to model EMG distribution plots stored in data memory 529. The comparison is based on standard correlation or comparison techniques known in the art. The model EMG distribution plots are based on either EMG activity of exceptionally healthy individuals or theoretical ideals. Typically, if EMG activity levels of individuals are used, the model EMG distribution plots of an individual is measured for a designated activity such as sports, labor, recreation, or health related activities. Based upon the comparison between the additional and model EMG distribution plots and upon previous comparisons, the microcontroller 524 calculates a trend. This trend indicates whether the user's EMG activity is improving toward the model. Subsequently, based on this trend and the feedback events, the microcontroller 524 furnishes an appropriate amount of feedback.

Typically, under this second approach, if the trend indicates that the user's EMG activity is continuing to approach the model, the microcontroller 524 will furnish feedback only in response to a fraction of the feedback events. This fraction typically ranges from ½ to ¹⁄₁₀ depending upon the user's characteristics and circumstances. Typically, if the user's EMG activity is staying the same or moving away from the model then the fraction will increase usually to 1. The amount of increase of the fraction can be adjusted as part of the threshold criteria downloaded into the data memory 529 according to the user's particular characteristics.

In the depicted embodiment, a procedure implemented in the microcontroller 524 of the EMG feedback monitor 110 to monitor surface EMG activity level of the user 140 and provide appropriate feedback is illustrated in FIG. 6. The procedure starts at step 610 and proceeds on to a sleep mode 612. In the sleep mode 612, the EMG feedback monitor 110 requires minimal amount of power from the battery 526. Little measurement and analysis activity is done in the sleep mode 612 by the EMG feedback monitor 110 except for periodic tests to determine whether the EMG feedback monitor should switch to an operational mode. These periodic tests are indicated by decision step 614 where the EMG feedback monitor 110 determines whether it should switch from the sleep mode 612 to an operational mode. In decision step 614, if a signal such as a reset signal or an interrupt signal is received by the microcontroller 524, the microcontroller switches from the sleep mode 612 into an operational mode. For instance, if the microcontroller 524 is reset, this would also cause the microcontroller to switch into an operational mode. A watchdog timer also is part of the microcontroller 524 in which after a preset time the controller resets which would also put the EMG feedback monitor 110 into an operational mode. Also, during the decision step 614, impedance levels of the electrodes 510–516 are measured and compared with a threshold by the microcontroller 524. This threshold level is typically 2 mega ohms for impedance and is measured with a small AC current being applied to the electrodes with resulting voltage being measured. If the impedance level drops below the threshold level, the EMG feedback monitor switches from the sleep mode 612 into the operational mode.

Once the microcontroller 524 determines to switch from the sleep mode 612 to the operational mode, the procedure branches under the "yes" condition of decision step 614 to step 616. If no conditions presently exist to cause the EMG feedback monitor 110 to switch from sleep mode 612 into operational mode, the decision step 614 branches under the "no" condition back to the sleep step 612. The decision step 614 is repeated periodically until the decision step 614 branches under the "yes" condition to step 616. In step 616, the red light status indicator 460 and green light power indicator 462 are flashed.

The procedure goes on to step 618 where self tests are performed by the microcontroller 524 and the test circuit 525 of the EMG feedback monitor 110. These self tests include another impedance measurement of the electrodes 510–516 using a threshold typically different than the wake up threshold used for impedance measurement of the decision step 614. The impedance tests of the electrodes 510–516 in step 618 indicate, among other things, whether the electrodes 510–516 are in place. The electrode impedance test of step 618 is also used to determine if the impedance of each signal electrode 510 and 512 with respect to ground is too high for proper operation at the EMG signal levels to be monitored. This test threshold is a programmable variable. It is measured the same as the "power on" impedance test used in determination step 614, but the impedance threshold is typically lower than the threshold used for the "power on" impedance test. Consequently, a short period of time may be required for the skin to absorb a sufficient amount of conductive cream to reach this lower impedance threshold. Use of conductive cream with electrodes to measure surface EMG activity level is well known in the art. A typical threshold level for impedance is below 2 mega ohms for detection while the device is in use. As stated, the EMG signal measured is in the microvolt range with a frequency of between 20 and 400 Hz. The operating impedance should have little effect on measurement of surface EMG activity level once it is within an acceptably low level. A high impedance on the other hand results in masking the lower levels of the EMG signals with noise.

A calibration test is included in the self tests of step 618. The calibration test involves a 200 microvolt AC test signal switched to the electrode inputs and furnished to the A to D converter 522 as an EMG signal to be measured. The A to D converter 522 converts the analog signal to a digital signal and the measured value of the digital signal is compared by the microcontroller 524 to stored high and low limits, which are typically plus or minus 5% of the applied 200 microvolt AC signal. If the measured value of the applied test signal is outside the stored high and low limits, the impedance test fails, otherwise, the impedance test passes. The criteria for passing varies among the other embodiments depending on the desired accuracy level of the electrodes.

Another self-test of step 618 tests a common mode rejection (CMR). Both of the signal electrodes 510 and 512 are switched to a same high level input signal, typically 1 volt AC. A resultant measured value is then compared by the microcontroller 524 to a stored high limit, which is typically 1 microvolt. Any voltage difference out of the input amplifier 518 greater than this 1 microvolt test limit results in a failed CMR test. However, if the voltage difference output from the input amplifier 518 is below the 1 microvolt test limit, the CMR test is passed.

The self-tests of step 618 also include a self-noise test where both electrode inputs of the signal electrodes 510 and 512 are switched to ground. The measured signal value is compared to a stored high limit, typically 1 microvolt, which if exceeded, fails the test; otherwise it passes the test. Also, in the depicted embodiment, the self-tests of step 618 include a battery test that measures voltage out of the battery 526 to determine whether there is sufficient power stored in the battery.

After all the tests are performed in step 618, the procedure moves to decision step 620 where the microcontroller 524 determines whether a time out has occurred. The time value typically for a time out is between 1 and 15 minutes. If a time out has occurred, the decision step 620 branches under the "yes" condition to step 622 where both red light status indicator 460 and green light power indicator 462 are turned off. After step 622, the procedure goes back to the sleep mode of step 612. If a time out has not occurred, the procedure branches under the "no" condition of the decision step 620 to decision step 624 to determine whether all the tests have been passed that were performed in step 618.

If not all tests of step 618 have been passed, the procedure branches under the "no" condition of the decision step 624 to step 626 to signal the user 140 via the red light status indicator 460 regarding the failed test. In the depicted embodiment, the red light status indicator 460 is flashed to signal the user 140 and the green light power indicator 462 is turned off in step 626, which then goes back to step 618 wherein tests are further performed. If all tests of step 618 are passed, the procedure under step 624 branches under the "yes" condition to step 628 where the red light status indicator 460 and green light power indicator 462 are set to signal the user 140 that the EMG feedback monitor 110 is in operational condition. In the depicted embodiment, the user 140 is signaled with the red light status indicator 460 turned off and the green light power indicator 462 slowly blinking. The green light continues to blink as long as the EMG feedback monitor 110 is in operational mode.

Step 628 then goes to step 630 where initialization is performed by the microcontroller 524 of the EMG feedback monitor 110. In the initialization step 630, the microcontroller 524 enters a ready status to begin collecting, analyzing, and storing data based on stored instructions related to the particular settings of the user control knob 450.

After initialization in step 630, the procedure moves to step 632 wherein data is collected of surface EMG activity level with the use of the electrodes 510–516, input amplifier 518, low pass filter 520 and A to D converter 522. The microcontroller 524 then performs digital filtering based on standard algorithms known in the art. The digital filtering rejects power line interference typically at 60 Hz and mechanical motion and vibration which is typically lower than 80 Hz. After collecting data in step 632 the EMG feedback monitor 110 goes onto step 634 where the data is analyzed. Hence, the microcontroller 524 performs functions including root mean square conversion and statistical analysis. Various results of the statistical analysis typically include details of the measured EMG signals related to average microvolt level, maximum microvolt level during a specified period of time, minimum microvolt level during the same specified period of time, percentage of time spent at given amplitude levels over a specified period of time called percent time amplitude, percentage of time satisfying a given threshold level, standard deviation and corrected standard deviation of the measured EMG signals, record of feedback occurrences, and mode switch settings of the user control knob 450. These details are used to characterize patterns of the surface EMG activity level, which is more effective than relying solely on raw data of surface EMG activity level.

Pattern information of surface EMG activity of the user 140 measured by the EMG feedback monitor 110 is helpful in remedial training of the user. For example, research shows that some people develop pain unless they spend a relatively small amount of time at a low level of surface EMG activity level. If only surface EMG activity values were recorded, rather than recording statistical information of the surface EMG activity as well, there may not be enough information to determine whether a person spent the requisite small amount of time at lower surface EMG activity levels, to avoid pain.

After the data is analyzed in step 634, the procedure goes to decision step 636 to determine whether the time since the last feedback event is greater than a predetermined interval. If the time is not greater than the predetermined interval, the decision step 636 branches under the "no" condition back to step 632 where more data is collected. If the time since the last feedback event is greater than the predetermined interval, the decision step 636 branches under the "yes" condition to decision step 638. In decision step 638, the microcontroller 524 of the EMG feedback monitor 110 determines whether the set of parameters related to threshold settings chosen via the user control knob 450 have been satisfied. These parameters are stored in the data memory 529 and include amount of time spent by the EMG signal above a predetermined threshold, whether the EMG signal satisfied a threshold level, time since the last feedback event, duration of feedback, percent of time that the EMG signal stayed at a certain amplitude, and the amount of standard deviation or corrected standard deviation of the EMG signal.

Depending on what set of parameters the user 140 has selected, the microcontroller 524 will then determine whether feedback is appropriate. If feedback is appropriate, decision step 638 branches under the "yes" condition to step 640 where the vibrator-motor 530 is activated to send a vibration signal to the user 140. After a predetermined time the vibrator-motor 530 is turned off and step 640 goes to step 642. If feedback is inappropriate, then the decision step 638 branches under the "no" condition to step 642 wherein data is saved to the data memory 529. In step 642, data is saved based on the current set of parameters chosen by the user 140 through the user control knob 450 and also based on what sets of parameters are downloaded into the EMG feedback monitor 110 by a therapist using the computer system 220 tied to the EMG feedback monitor 110 through the computer interface cable 230. The data saved would typically be the same as the results of the analysis performed in step 634 on the EMG signals.

After data is saved in step 642, the procedure goes to decision step 644 to determine whether the user 140 has selected another set of parameters with the user control knob 450. If the user 140 has selected a different set of parameters to be implemented by the EMG feedback monitor 110, the procedure branches under the "yes" condition back to step 630 where initialization is again performed. If the user 140 has not changed to another set of parameters, the decision step 644 branches under the "no" condition to step 646 where another impedance test is performed. The impedance test in step 646 is the same as the impedance test performed in the self-tests of step 618. The impedance test is performed again in step 646 to ensure that the condition of the electrodes is still acceptable. After the impedance test is performed in step 646, the procedure goes to decision step 648 to determine whether the impedance test has been passed. If the impedance test has been passed, the decision step 648 branches under the "yes" condition back to step 632 where more EMG signal data is collected. If the impedance test performed in step 646 is not passed, decision step 648 branches under the "no" condition back to step 612 where the EMG feedback monitor 110 switches back to the sleep mode.

Figure 7:
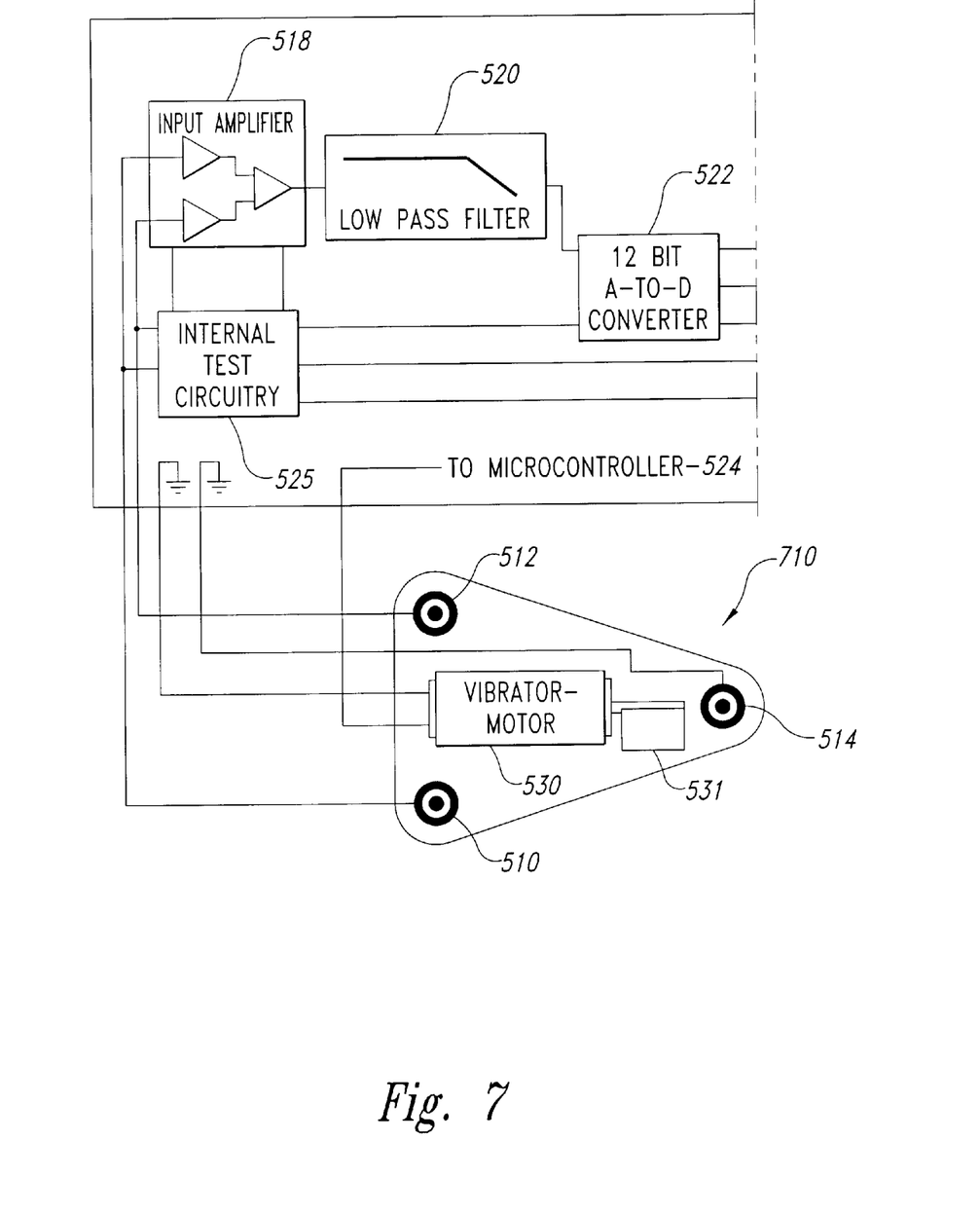
FIG. 7 is a block diagram showing detail of a sensor/feedback package of an alternative embodiment of the invention of FIG. 1.

In an alternate embodiment, the vibrator-motor 530 and weight 531 are located with the electrodes 510, 512, and 514 in a sensor/feedback package 710. The sensor/feedback package 710 is separate from the housing 120 of the EMG feedback monitor 110 as shown in FIG. 7. The housing 120 still contains all the other components of the EMG feedback 110 previously discussed. The electrodes 510, 512, and 514 and the vibrator-motor 530 are still electrically connected to the same components of the EMG feedback monitor 110. The signal electrodes 510 and 512 are connected to the input amplifier 518. The ground electrode 514 is connected to a common ground of the EMG feedback monitor 110. The vibrator-motor 530 is connected to the microcontroller 524 and ground. In this case, the electronic connections are provided through an external electrical cable. The rest of the EMG feedback monitor 110 including the housing 120 is still worn by the user 140 in a location other than the monitored location.

The sensor/feedback package 710 is used to locate the electrodes 510–514 in regions of the body of the user 140 where comfort issues would exclude placement of the housing 120 of the EMG feedback monitor 110. Since the vibrator-motor 530 and weight 531 are co-located with the electrodes 510–514, tactile feedback is still administered to the monitored region of the body of the user 140. Applying tactile feedback to the monitored region through the sensor/feedback package 710 maintains the direct association between feedback and the condition being monitored even when the housing 120 is located in a region of the body of the user 140 other than the monitored region.

Figure 8A:
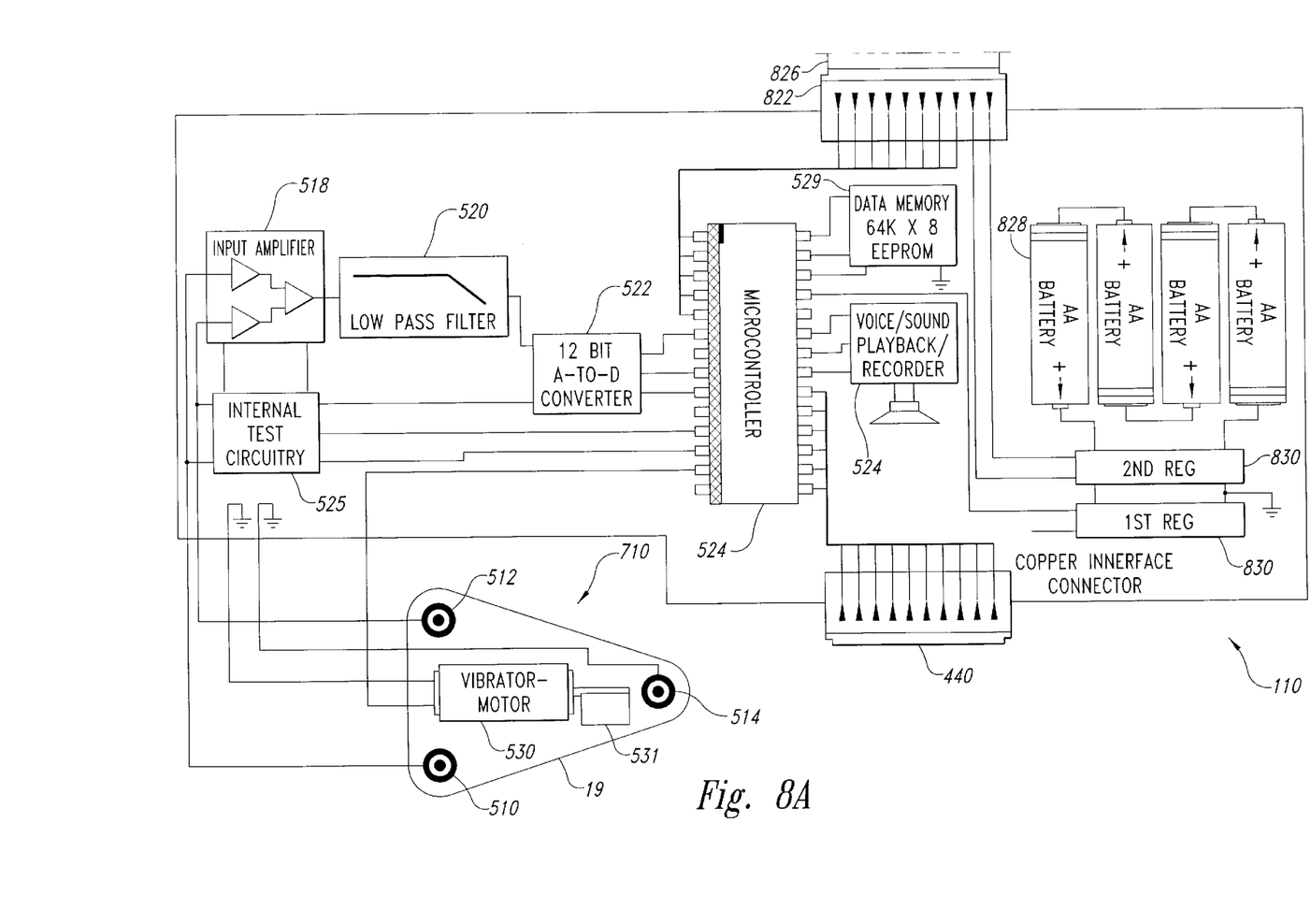
FIG. 8 is a block diagram of an alternative embodiment of the invention of FIG. 1.
Figure 8B:
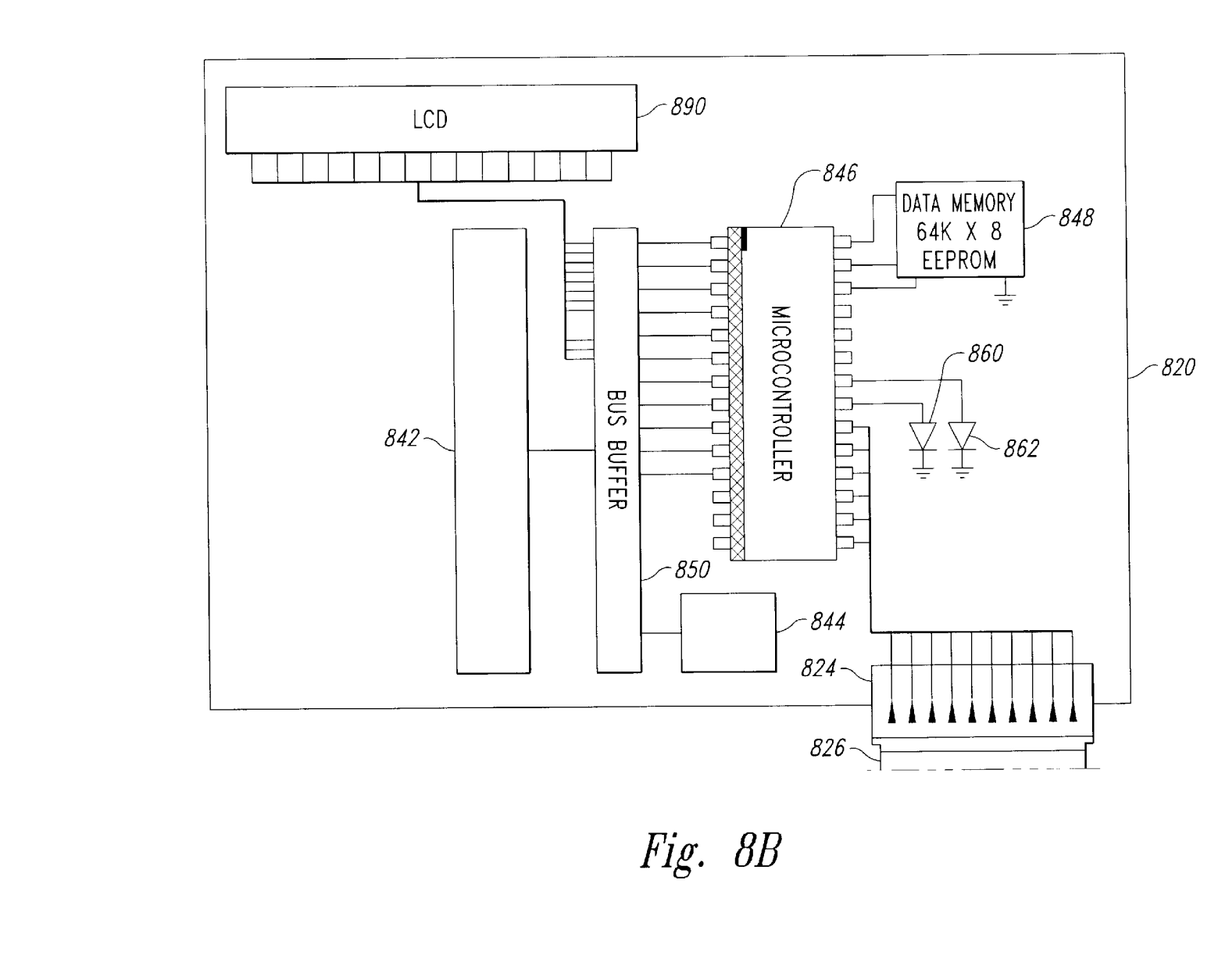

In another embodiment, visual and audio feedback is provided in addition to tactile feedback. In this embodiment, as shown in FIG. 8, the EMG feedback monitor 110 is divided into three sections: the sensor/feedback package 710, the master module 818, and the slave module 820. The master module 818 is connected to the slave module 820 via master connector 822, slave connector 824, and master-slave connector cable 826 as shown in FIG. 8. The master module 818 has most of the components of the EMG feedback monitor 110 except that in this case, the master module has a larger capacity power source 828, a first regulator 830 to regulate power to the microcontroller 524 and a second power regulator 832 to regulate power to the slave module 820. In addition, the master module 818 also includes a voice/sound playback/recorder 834. The audio output of the voice/sound playback/recorder 834 indicates surface EMG activity either by predefined tones or prerecorded voice. The prerecorded voice provides additional feedback in that voice prompts can be used to instruct the user regarding their behavior and operation of the EMG feedback monitor 110. The voice/sound playback/recorder 834 is also used to record tones or voice prompts.

The slave module 820 includes an LCD display 840 and a bar graph 842 which supply text and visual feedback, respectively, to the user 140. A keyboard 844 allows the user 140 to input commands or query the EMG feedback monitor 110. A microcontroller 846 located in the slave module 820 handles processing of the display outputs and keyboard inputs. A memory storage device 848 is connected to the microcontroller to store data and instructions used by the microcontroller. A red light status indicator 860 and a green light power indicator 862 are also located in the slave module 820.

The configuration shown in FIG. 8 allows flexibility of use in that the sensor/feedback package 710, the master module 818 and slave module 820 can be located in separate regions on the user 140. For instance, the sensor/feedback package 710 can be located on a region of the user 140 to be monitored. The master module 818 can be worn on the user 140 in a location other than the monitored region to allow for better fit and greater comfort. The slave module 820 can be either worn by the user 140 or located somewhere else such as on a table top. In this alternate embodiment, the visual feedback and keyboard input is optional so that the user 140 also monitors EMG activity level without the slave module 820. In another alternative embodiment, the master module 818 and slave module 820 communicate with one another via a wireless communication link.

All of the above U.S. patents and applications are incorporated by reference. While the depicted embodiment is used in training and rehabilitation for health conditions, other embodiments of the invention can be similarly used for monitoring and providing feedback related to other objectives, such as, for example, sports related activities, scientific research, or business activities. Furthermore, aspects of the embodiments disclosed in the commonly assigned, concurrently filed and co-pending U.S. applications referenced above can be combined with aspects of the embodiments disclosed herein. For instance, aspects of the Respiration Feedback Monitor System could be combined with aspects disclosed herein resulting in a feedback monitor for a user's respiration and muscle activities. As an alternative example, aspects of the Heart Rate Variability Feedback Monitor System could be combined with aspects disclosed herein resulting in a feedback monitor for a user's heart and muscle activities.

These and other changes can be made to the invention in light of the above-detailed description. In general, in the following claims, the terms should not be construed to limit the invention to specific embodiments disclosed in the specification and the claims, but should be construed to include all wearable EMG feedback monitors that operate under the claims to provide a wearable system for monitoring and providing appropriate feedback related to surface EMG activity of a user. Accordingly, the invention is not limited by the disclosure, but instead its scope is to be determined entirely by the following claims.

What is claimed is:

1. An electromyographic monitor system for a user, the system comprising:

a sensor package sized and configured to be worn by the user;

a plurality of electromyographic electrodes affixed to the sensor package, the electromyographic electrodes configured to produce electromyographic signals based on surface electromyographic activity of a monitored region of the user;

a vibration output device affixed to the sensor package, the vibration output device configured to transmit to the monitored region of the user a vibration signal perceptible by the user when the output device is activated;

a processor configured to receive digital signals associated with the electromyographic signals produced by the plurality of electromyographic electrodes, the electrodes measuring electromyographic activity of the user, the processor configured to transmit a signal to activate the vibration output device based on whether the measured electromyographic signals satisfy electromyographic feedback criteria wherein the electromyographic feedback criteria are related to electromyographic signal levels and time measurements associated with the measured electromyographic signals; and a user control coupled to the processor wherein the user with the user control selects an operational mode having a particular electromyographic feedback criteria from a plurality of operational modes under which the processor operates.

2. The electromyographic monitor system of claim 1, further including:
a housing wherein the sensor package is an integral part of the housing and the vibration output device and the processor are affixed to the housing.

3. The electromyographic monitor system of claim 1 wherein the processor is further configured to adjust the electromyographic feedback criteria of the selected operational mode based on the measured electromyographic signals.

4. The electromyographic monitor system of claim 1 wherein the plurality of operational modes comprises: Percent Time Amplitude Mode, Threshold Amplitude Mode, Median Frequency Mode, Prompted Exercise Mode, or Threshold Shaping Mode.

5. The electromyographic monitor system of claim 1, further including:
a housing wherein the processor is affixed to the housing and the electromyographic signals are sent from the sensor package to the housing by an electrical cable external to the housing; and
a slave output electrically coupled to the processor by an electrical cable external to the housing.

6. The electromyographic monitor system of claim 1, further including:
a housing wherein the processor is affixed to the housing and the electromyographic signals are sent from the sensor package to the housing by an electrical cable external to the housing; and
a slave output electrically coupled to the processor by a wireless communication link.

7. The electromyographic monitor system of claim 1, further comprising:
a connector configured to detachably connect the electromyographic feedback monitor system to a computer system via an interface cable wherein the computer system transmits electromyographic feedback criteria to the electromyographic feedback monitor system.

8. The electromyographic monitor system of claim 1, further including:
a housing sized and configured to contain the processor and the user control.

9. An electromyographic monitor system for a user, the system comprising:
an output device configured to be worn by the user and to transmit a signal perceptible by the user when the output device is activated;
a memory storing electromyographic feedback criteria; and
a processor electrically coupled to the output device and the memory, the processor configured to receive digital signals associated with electromyographic signals indicating electromyographic activity of the user, the processor configured to transmit an activation signal to activate the output device based on whether the measured electromyographic signals satisfy the electromyographic feedback criteria stored in the memory.

10. The electromyographic monitor system of claim 9 wherein the processor and memory are monolithically integrated on the same integrated circuit.

11. The electromyographic monitor system of claim 9 wherein the output device is a vibrator configured to transmit vibrations to a monitored region of the user to be perceived by the user.

12. The electromyographic monitor system of claim 9, further comprising:
a housing wherein the processor is affixed to the housing and the output device and the processor are electrically coupled by an electrical cable external to the housing.

13. The electromyographic monitor system of claim 9 wherein the electromyographic feedback criteria are related to electromyographic signal levels and time measurements associated with the measured electromyographic signals.

14. The electromyographic monitor system of claim 9 wherein the output device emits audio tones or voice prompts, or displays bar graphs or text.

15. The electromyographic monitor system of claim 9 wherein the electromyographic feedback criteria are associated with data comprising maximum microvolt level of the measured electromyographic signals during a specified period of time, minimum microvolt level of the measured electromyographic signals during a specified period of time, percentage of time that the measured electromyographic signals spend at given amplitude levels over a specified period of time, percentage of time that the measured electromyographic signals are above a given threshold level, percentage of time that the measured electromyographic signals are below a given threshold level, standard deviation of the measured electromyographic signals, number of feedback occurrences, duration of feedback, or EMG distribution plots.

16. The electromyographic monitor system of claim 9 wherein the processor is further configured to adjust the electromyographic feedback criteria based on the measured electromyographic signals.

17. The electromyographic monitor system of claim 9 wherein the processor has a sleep mode and an operational mode, the processor configured to determine impedance levels of the electrodes and configured to switch from the sleep mode to the operational mode based on the impedance levels of the electrodes.

18. The electromyographic monitor system of claim 9 wherein the housing has a height of less than 4 inches, a width of less than 4 inches and a depth of less than 2 inches.

19. The electromyographic monitor system of claim 9 wherein the housing has an outer surface and the electrodes are integrally affixed to the outer surface of the housing.

20. The electromyographic monitor system of claim 9 wherein the processor is further configured to analyze the digital signals regarding signal levels and associated time measurements of the measured electromyographic signals.

21. The electromyographic monitor system of claim 9 wherein the processor is configured to perform fault detection comprising calibration of the electrodes, determining common mode rejection of a differential amplifier, or determining self-noise of the electromyographic feedback monitor system.

22. The electromyographic monitor system of claim 9, further including a user control wherein the user selects with the user control an operational mode from a plurality of operational modes under which the processor operates, the plurality of operational modes comprising Percent Time Amplitude Mode, Threshold Amplitude Mode, Median Frequency Mode, Prompted Exercise Mode, or Threshold Shaping Mode.

23. The electromyographic feedback monitor system of claim 9 wherein the electromyographic feedback criteria are associated with the time domain or frequency domain calculations associated with the measured electromyographic signals.

24. The electromyographic feedback monitor system of claim 9 wherein the processor determines trend and transmits the activation signal further based on the trend.

25. An electromyographic monitor system for a user, the system comprising:
a housing configured to be worn by the user;
a storage device affixed to the housing, the storage device configured to store electromyographic signal data of electromyographic signals received from electrodes;
a communication link configured to provide signals from the electromyographic monitor system to a computer system wherein the signal data are transferred to the computer system; and
a user control wherein the user selects with the user control an operational mode from a plurality of operational modes stored in the storage device, the processor performing according to parameters associated with the selected operational mode.

26. An electromyographic monitor system for a user, the system comprising:
a housing configured to be worn by the user;
a memory storing electromyographic feedback criteria;
a processor affixed to the housing configured to receive digital signals associated with electromyographic signals measured by electrodes, the processor configured to turn on an output device based on the electromyographic feedback criteria stored in the memory associated with the measured electromyographic signals; and
a communication link configured to provide signals from a system computer to the electromyographic feedback monitor system to a computer system wherein the computer system is configured to adjust the electromyographic feedback criteria stored in the memory.

27. The electromyographic monitor system of claim 26, further including a user control wherein the user selects electromyographic feedback criteria stored in the memory.

28. The electromyographic monitor system of claim 26 wherein the electromyographic feedback criteria includes Percent Time Amplitude Mode, Threshold Amplitude Mode, Medium Frequency Mode, Prompted Exercise Mode, or Threshold Shaping Mode.

29. The electromyographic monitor system of claim 26 wherein the output device is electrically coupled to the processor by an electrical cable external to the housing.

30. The electromyographic monitor system of claim 26 wherein the communication link is a cable.

31. The electromyographic monitor system of claim 26 wherein the communication link is wireless.

32. The electromyographic monitor system of claim 26 wherein the output device outputs a tactile signal.

33. A method comprising:
assigning parameter values for a plurality of operational modes associated with an electromyographic feedback monitor system;
selecting an operational mode from the plurality of operational modes;
measuring electromyographic signals associated with electromyographic activity in a monitored region of the user;
analyzing the electromyographic signals based on the selected operational mode; and
transmitting a tactile signal to the monitored region of the user perceptible by the user based upon results of the analysis.

34. The method of claim 33 wherein analyzing is performed in a location other than the monitored region.

35. The method of claim 33, further including:
adjusting electromyographic feedback criteria associated with the plurality of operational modes based upon results of the analysis.

36. The method of claim 33, further including:
transmitting a visual or audio output based upon results of the analysis.

* * * * *